(12) United States Patent

Malinin (10) Patent No.: US 8,916,339 B1
(45) Date of Patent: Dec. 23, 2014

(54) SPINAL CORD TISSUE DEHYDRATED AND MICRONIZED

(71) Applicant: Theodore I. Malinin, Key Biscayne, FL (US)

(72) Inventor: Theodore I. Malinin, Key Biscayne, FL (US)

(73) Assignee: Vivex Biomedical, Inc., Marietta, GA (US)

( * ) Notice: Subject to any disclaimer, the term of this patent is extended or adjusted under 35 U.S.C. 154(b) by 0 days.

(21) Appl. No.: 14/200,729

(22) Filed: Mar. 7, 2014

Related U.S. Application Data

(60) Provisional application No. 61/898,141, filed on Oct. 31, 2013.

(51) Int. Cl.
| | |
|---|---|
| *A61K 51/00* | (2006.01) |
| *A61M 36/14* | (2006.01) |
| *A61K 35/30* | (2006.01) |
| *A61K 38/17* | (2006.01) |
| *A61K 9/00* | (2006.01) |

(52) U.S. Cl.
CPC ............ *A61K 35/30* (2013.01); *A61K 38/17* (2013.01); *A61K 9/0019* (2013.01); *A61K 9/0024* (2013.01); *A61K 9/0085* (2013.01)
USPC .............. 435/1.3; 435/1.1; 424/423; 424/570

(58) Field of Classification Search
CPC . A61K 9/0024; A61K 9/0085; A61K 31/717; A61K 35/30; A61K 38/17; A61K 9/0019; C12N 5/06; C12N 5/0619; C12N 11/04; C12N 11/08; C12N 5/0012; C12N 5/0622; C12N 5/0623; C12N 5/0677; A01K 2217/05
See application file for complete search history.

(56) References Cited

U.S. PATENT DOCUMENTS

| | | | |
|---|---|---|---|
| 6,020,197 | A | 2/2000 | Gage et al. |
| 6,040,180 | A | 3/2000 | Johe |
| 2009/0087851 | A1 | 4/2009 | Rao et al. |
| 2011/0076256 | A1 | 3/2011 | Park |
| 2011/0217774 | A1 | 9/2011 | Kim et al. |
| 2012/0107284 | A1 | 5/2012 | Kozlova |
| 2012/0171722 | A1 | 7/2012 | Deisher |
| 2013/0157365 | A1 | 6/2013 | Buensuceso et al. |
| 2013/0252335 | A1 | 9/2013 | Kume et al. |

FOREIGN PATENT DOCUMENTS

| | | |
|---|---|---|
| JP | 2010051326 | 11/2010 |
| WO | 9301275 | 1/1993 |

OTHER PUBLICATIONS

Beuls et al. Microanatomy of the Excised Human Spinal Cord and the Cervicomedullary Junction Examined with High-Resolution MR Imaging at 9.4 Tesla. American Journal of Neuroradiology, 1993, vol. 14, pp. 699-707.*
Kato et al. Choline Acetyltransferase Activities in Single Spinal Motor Neurons from Patients with Amyotrophic Lateral Sclerosis. Journal of Neurochemistry, 1989, vol. 52, pp. 636-640.*
Lowry et al. The Quantitative Histochemistry of the Brain. Journal of Histochemistry and Cytochemistry, 1953, vol. 1, pp. 420-428.*
Kutlay et al. Effect of Hyperbaric Oxygen Treatment on Fetal Spinal Cord Grafts: A Preliminary Experimental Study. Turkish Neurosurgery, 2000, vol. 10, pp. 90-102.*
Teng et al. Functional recovery following traumatic spinal cord injury mediated by a unique polymer scaffold seeded with neural stem cells. PNAS, 2002, vol. 99, pp. 3024-3029.*
Mokry et al. Biocompatibility of HEMA Copolymers Designed for Treatment of CNS Diseases with Polymer-Encapsulated Cells. Biotechnological Progress, 2000, vol. 16, pp. 897-904.*
Leung et al. Plasma expanders stabilize human microvessels in microfluidic scaffolds. J Biomed Mater Res Part A 2012:100A:1815-1822.*
Barradas, Ana M.C., et al; "Osteoinductive Biomaterials: Current Knowledge of Properties Experimental Models and Biological Mechanisms"; European Cells and Materials vol. 21, 2011 (pp. 407-429).
Du K, et al; "Expression of the Stem Cell marker Nestin in Pre/Hypertorphic Chondrocytes in Osteochondroma"; Journal of International Medical Research 2011 39: 348.
Ligon, KL, et al; "Olig Gene Function in CNS Development and Disease", published online May 1, 2006 in Wiley InterScience (www.interscience.wiley.com). GLIA 54:1-10.
Mekki-Dauriac, S, et al; "Bone Morphogenetic proteins negatively control oligodendrocyte precursor specification in the chick spinal cord"; Development 129, 5117-5130(2002).
Morris, SA, et al; "A blueprint for engineering cell fate: current technologies to reprogram cell identity"; Cell Research (2013) 23:33-48.
Ortega-Martinez, M, et al; "Evidence of chondrocyte turnover in lung cartilage, with the probable participation of nestin-positive cells"; Cell Biology International ISSN 1065-6995, 2013.
Peljto, M, et al; "Programming embryonic stem cells to neuronal subtypes"; Current Opinion in Neurobiology 2011, 21: 43-51.
Reddi, A.H.; "Implant-stimulated interface reactions during collagenous bone matrix-induced bone formation"; Journal of Biomedical Materials Research, vol. 19, 233-239 (1985).
Urist, M.R.; "Bone: Formatoin by Autoinduction"; Science, New Series, vol. 150, No. 3698 (Nov. 12, 1965) pp. 893-899.
Urist, M.R.; "Bone Morphogenetic Protein: The Molecularization of Skeletal System Development", Journal of Bone and Mineral Research, vol. 12, No. 3, 1997, Blackwell Science Inc.
Wang, Y, et al; "A transcriptional roadmap to the induction of pluripotency in somatic cells"; Stem Cell Rev and Rep (2010) 6:282-296.
Wiese, C., et al; "Nestin expression—a property of multi-lineage progenitor cells?"; CMLS, Cell. Mol. Life Sci. 61 (2004) 2510-2522.
Wu, R, et al; "Derivation of multipotent nestin +/CD271-/STRO-1-mesenchymal-like precursors from human embryonic stem cells in chemically defined conditions"; Human Cell (2013) 26: 19-27.

* cited by examiner (Continued)

*Primary Examiner* — Deborah Crouch
(74) *Attorney, Agent, or Firm* — David L King (57) ABSTRACT

A composition of neural tissue is made of spinal cord tissue harvested from a spinal cord of a mammal. The spinal cord tissue is harvested from vertebral column of the mammal. The spinal cord tissue is harvested post mortem. The mammal is one of a primate, an equine, a bovine, a porcine or other mammalian animal. The spinal cord tissue is dried or has the water content in the tissue reduced or eliminated by freeze drying or hypothermic dehydration.

27 Claims, 6 Drawing Sheets

SPINAL CORD TISSUE DEHYDRATED AND MICRONIZED

FIELD OF THE INVENTION

This application relates to a composition made with spinal cord tissue as at least a component.

BACKGROUND OF THE INVENTION

Nerve damage and degenerative nerve conditions affect those suffering from these conditions tremendously, depending on the severity of the symptoms. Traumatic injuries are a leading cause of nerve and spinal cord damage that can vary from minor self-healing to more severe symptoms such as constant pain up to complete loss of feeling or even paralysis. When nerves are cut, complete loss of electrical signals occurs. Similarly, neurological disorders involving neural cells are common among stroke victims wherein electrical signals evidencing brain activity in regions of the brain is lost.

Degenerative conditions in the brain and the nerves generally can cause similar loss of electrical activity in these tissues.

Efforts to reduce these symptoms or to repair, regenerate and reactivate cellular functioning of damaged or degenerative conditions is a priority in medicine. To date, application of autologous cells met with only limited success. The present invention discloses induction of nerve cells without participation of viable cells.

SUMMARY OF THE INVENTION

A composition of neural tissue is made of spinal cord tissue harvested from a spinal cord of a mammal. The spinal cord tissue is harvested from vertebral column of the mammal. The spinal cord tissue is harvested post mortem. The mammal is one of a primate, an equine, a bovine, a porcine or other mammalis. The spinal cord tissue is dried or has the water content in the tissue reduced or eliminated, preferably by freeze drying or hypothermic dehydration. In one embodiment, the spinal cord had been washed in lactated Ringer's Solution or other balanaced salt solution and placed into a vapor phase of liquid nitrogen. The frozen spinal cord was then transferred to a freeze dryer chamber with vacuum below 100 millitors for three days or until desired residual water level is reached after which the freeze dryer was heated to room temperature and the vacuum released to form a freeze dried spinal cord. The spinal cord tissue was cut into pieces from freeze dried spinal cord segments to form freeze dried spinal cord tissue pieces. The pieces of the freeze dried spinal cord tissue were ground to form freeze dried spinal cord tissue micronized particles or cut or chopped to form freeze dried spinal cord tissue strands or fragments. In one embodiment, the freeze dried spinal cord tissue micronized particles have a particle size greater than 50 microns; preferably the particle size of the micronized particles is about 100 to about 400 microns. In another embodiment, the strands or fragments have a length in the range of 1 to 6 mm; preferably, the length of the strands or fragments is about 2 to 4 mm.

In one embodiment, the primate is a human. The human post mortem spinal cord was excised aseptically without dura mater from the cadaver donor. In at least one embodiment, the freeze dried spinal cord tissue micronized particles or strands or fragments were prepared aseptically and sterile packaged in dose sized quantities and stored at room temperature.

The composition of dried spinal cord tissue micronized particles or strands or fragments or combinations thereof are intended to be implanted into human recipients having neural cell or nerve damage and after implantation initiates a cellular response of host cells and a reprogramming of host cells. In experimental animals, the host cells infiltrate the composition and spread throughout the composition to form infiltrating host cells. The infiltrating host cells exhibit and express nestin, Olig2 and beta-III tubulin markers with the capacity to initiate differentiation into neuronal or glial lineages. Also, the infiltrating host cells associated with the implanted composition have no expression of the marker Sox9 for osteogenic differentiation. The composition of the freeze dried spinal cord tissue is processed to form an acellular material composition with the capacity to induce reprogramming of host cells into specific neural lineages.

The dried micronized spinal cord tissue when used as an implant transforms host cells to express neural lineage markers in the absence of forced reprogramming of host cells by expressed transcription factor needed to drive neural differentiation. The composition of the freeze dried or dried by other means spinal cord tissue when used in an implant can be used as a neural treatment for repair of brain injury due to trauma or stroke or as a neural treatment for degenerative neural conditions. The implant is intended to be used to promote repair of nerve damage or to stimulate new nerve growth or both.

In one embodiment, the spinal cord tissue was embedded in hydroxy-ethyl starch to avoid dispersion. The fragments were freeze dried and were embedded in a bioabsorbable material for implantation by way of example. The bioabsorbable material could be a hydroxide starch or other bioabsorbable material such as polyvinyl pyrolidone, albumin, dextran, or equivalents thereof. The spinal cord tissue can be prepared by dehydration at hypothermic temperatures by chemical dehydration or any other method. Preferably, the composition is rehydrated prior to implantation and can be implanted as a colloidal suspension in a liquid, a paste or an element or component of a bioabsorbable implant material.

BRIEF DESCRIPTION OF THE DRAWINGS

The invention will be described by way of example and with reference to the accompanying drawings in which:

FIGS. 1A and 1E are a low magnification and FIGS. 1B and 1F are at high magnification. FIGS. 1A and 1B after 2 weeks. Figures 1E and 1F after 4 weeks.

DETAILED DESCRIPTION OF THE INVENTION

The term "about" as used herein may be applied to modify any quantitative representation which could permissibly vary without resulting in a change in the basic function to which it is related.

Figure 6:
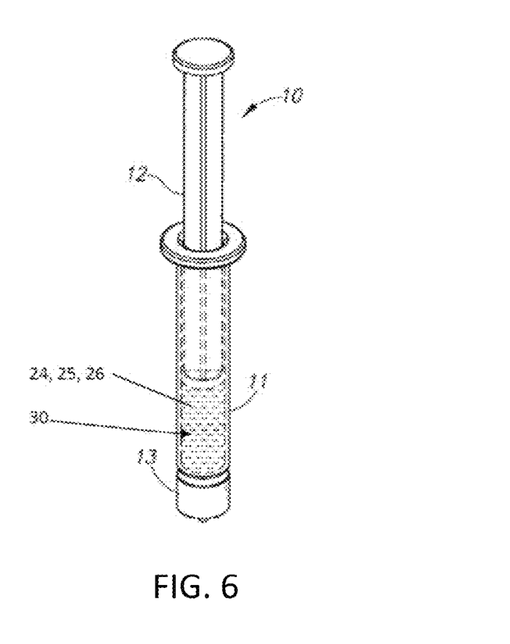
FIG. 6 is an exemplary first embodiment showing an exemplary composition in a syringe device.
Figure 7:
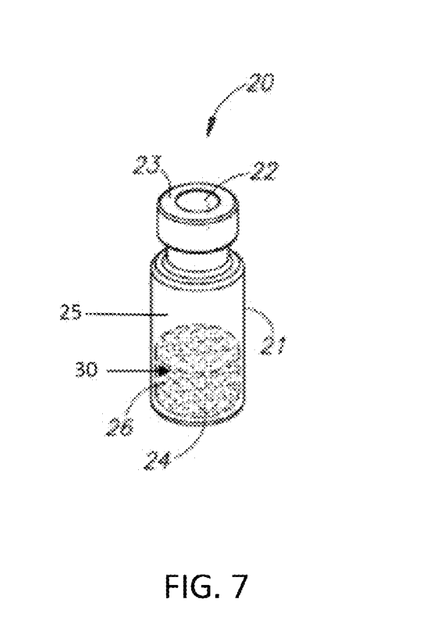
FIG. 7 is an exemplary second embodiment showing an exemplary composition in a container.
Figure 8A:
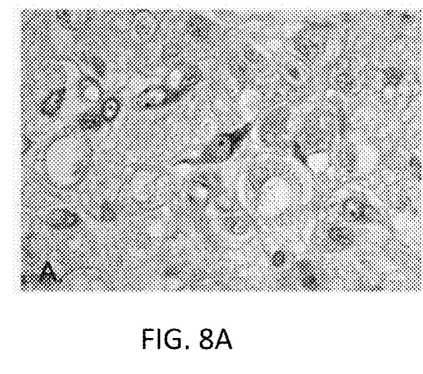
FIGS. 8A-8D are histological pictures of newly formed tissue induced by the spinal cord particles of the present invention.
Figure 8B:
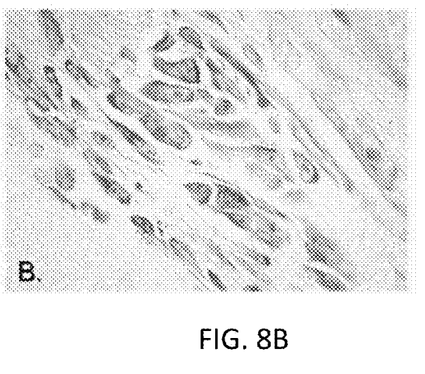
Figure 8C:
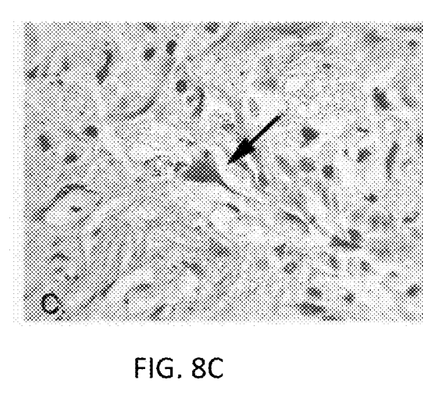
Figure 8D:
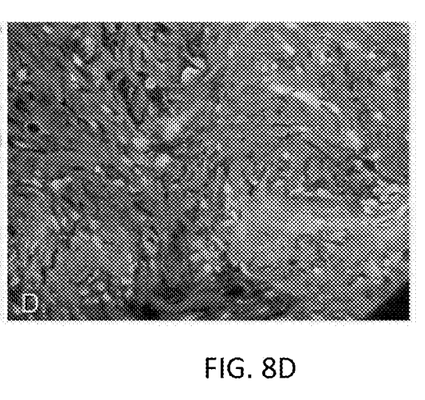

With reference to FIGS. 6 and 7, an exemplary composition 30 according to the present invention is shown in exemplary storage and delivery devices. In FIG. 6, a syringe device 10 is illustrated. The syringe has a plunger 12, a syringe housing body 11 and a dispensing end 13 for delivering the composition 30 through a nozzle end or similar opening. In storage, the syringe 10 is preferably sealed and isolated from the external environment. The composition 30 may be composed of micronized particles 24 or strands 25 or fragments 26 of spinal cord tissue or any combination thereof. The composition 30 may be stored as a pure composition of any one of the elements, micronized particles 24, strands 25 or fragments 26 or any combination thereof. Prior to implantation, the composition 30 which can be freeze dried spinal cord tissue stored dry can be rehydrated with saline, water or dextrose or any suitable hydrating liquid. Alternatively, the composition 30 can be mixed or embedded in a bioabsorbable material such as a hydroxy-ethyl starch or suitable carrier material and applied as an implant in solid or paste or gel-like consistency to rehydrate without otherwise altering the properties of the spinal cord tissue. In FIG. 7, the composition 30 is shown stored in a vial or small container 20 as another optional delivery and storage device. These alternatives are not intended to be limiting, but simply exemplary of the need to seal the composition 30 prior to use and to avoid contact with moisture or humidity prior to actual use. The vial 20 has an end closure 23 with a stopper 22 and a container 21 into which the micronized particles 24, strands 25 or fragments 26 or any combination thereof can be stored. The devices are such that treatment dosages can be held. In FIG. 7, the space above the composition 30 preferably can be evacuated.

The composition 30 in the vial 20 is a composition including or having neural tissue. The composition has spinal cord tissue harvested from a mammal. The spinal cord tissue is dried or has the water content reduced or eliminated. This can be accomplished in a number of ways such as dehydration at hypothermic temperatures, by freeze drying or by chemical dehydration of the spinal cord tissue. The spinal cord, once freeze dried, can be cut into pieces or strips. After which, the pieces or strips can be ground to form freeze dried spinal cord tissue micronized particles 24. Alternatively, the pieces or strips can be cut or chopped to form freeze dried spinal cord tissue strands 25 or fragments 26.

A composition of neural tissue is made of spinal cord tissue harvested from a spinal cord of a mammal. The spinal cord tissue is harvested from vertebral column of the mammal. The spinal cord tissue is harvested post mortem. The mammal is one of a primate, an equine, a bovine, a porcine or other mammalian animal. The spinal cord tissue is dried or has the water content in the tissue reduced or eliminated, preferably by freeze drying or hypothermic dehydration. In one embodiment, the spinal cord had been placed in lactated Ringer's Solution or other suitable fluid and placed into a vapor phase of liquid nitrogen and the frozen spinal cord was transferred to a freeze dryer under vacuum for three days after which the freeze dryer was heated to room temperature and the vacuum released to form a freeze dried spinal cord. Alternatively, the tissue can be frozen in mechanical freezers. The spinal cord tissue was cut into pieces from a freeze dried spinal cord to form freeze dried spinal cord tissue pieces. The pieces of the freeze dried spinal cord tissue were ground to form freeze dried spinal cord tissue micronized particles or cut or chopped to form freeze dried spinal cord tissue strands or fragments. In one embodiment, the freeze dried spinal cord tissue micronized particles have a particle size greater than 50 microns; preferably the particle size of the micronized particles is about 100 to about 400 microns. In another embodiment, the strands or fragments have a length in the range of 1 to 6 mm; preferably, the length of the strands or fragments is about 2 to 4 mm.

In one embodiment, the primate is a human. The human post mortem spinal cord was excised aseptically without dura mater from the cadaver donor. In at least one embodiment, the freeze dried spinal cord tissue micronized particles or strands or fragments were prepared aseptically and sterile packaged in dose sized quantities and stored at room temperature.

The composition of freeze dried spinal cord tissue micronized particles or strands or fragments or combinations thereof are intended to be implanted into human recipients having neural cell or nerve damage and after implantation initiates a cellular response of host cells and a reprogramming of host cells. The host cells infiltrate the composition and spread throughout the composition to form infiltrating host cells. The infiltrating host cells exhibit and express nestin, Olig2 and beta-III tubulin markers with the capacity to initiate differentiation into neuronal or glial lineages. Also, the infiltrating host cells associated with the implanted composition have no expression of the marker Sox9 for osteogenic differentiation. The composition of the freeze dried spinal cord tissue is processed to form an acellular material composition with the capacity to induce reprogramming of host cells into specific neural lineages.

The freeze dried spinal cord tissue when used as an implant transforms host cells to express neural lineage markers in the absence of forced reprogramming of host cells by expressed transcription factor to needed to drive neural differentiation. The composition of the freeze dried spinal cord tissue when used in an implant can be used as a neural treatment for repair of brain injury due to trauma or stroke or as a neural treatment for degenerative neural conditions. The implant can be used to promote repair of nerve damage or to stimulate new nerve growth or both.

In one embodiment, the spinal cord tissue was provided as fragments. The fragments were freeze dried and were embedded in a bioabsorbable material for implantation by way of example. The bioabsorbable material could be a hydroxy-ethyl starch. The spinal cord tissue can be prepared by dehydration at hypothermic temperatures. Preferably, the composition is rehydrated prior to implantation and can be implanted as a colloidal suspension in a liquid, a paste or an element or component of a bioabsorbable implant material.

The osteoinductive capacity of biological non-cellular material using demineralized bone matrix has demonstrated that host mesenchymal cells can be transformed into osteoprogenitors and chondrogenic cells by exposure to residual bone morphogenetic proteins in demineralized and non-demineralized bone matrix. The present inventive concept is a composition of biological non-cellular material of micronized human spinal cord tissue. This composition has been found to induce transformation of host cells into a neural lineage cells. The expression of neural-specific lineage markers in host cells colonizing implanted spinal cord tissue, along with the lack of expression of chondrocyte and osteogenic lineage markers has been achieved. These studies demonstrate that the inductive capacity of biological non-cellular material is not limited to the osteogenic lineage, but that acellular spinal cord tissue could be used to generate host-derived cells for use in neural repair and regeneration.

The inductive capacity of biological non-cellular material such as bone has been recognized for over fifty years. Urist (1965) demonstrated that cell-free demineralized bone matrix was capable of recruiting mesenchymal cells to undergo a cascade of events leading to the differentiation and maturation of osteoprogenitors resulting in the eventual deposition and remodeling of new bone. This observation, and the subsequent recognition that bone morphogenetic proteins were key factors in stimulating this induction, has led to the extensive surgical use of cell-free demineralized bone matrix to stimulate bone regeneration and remodeling in vivo.

However, non-demineralized non-viable particulate bone also causes mesenchymal cells to transform into osteoprogenitor cells and so does cartilage. The finding that mesenchymal cells could be reprogrammed in vivo into the osteogenic and chondrogenic lineage contributed to the recognition that fate changes in somatic cells could be induced by the right combination of signals. This was conclusively demonstrated by the generation of induced pluripotent stem (iPS) cells from fibroblasts by the forced expression of small sets of transcription factors.

Like embryonic stem cells, iPS cells can adopt a wide range of cell fates. However, unlike the direct recruitment of mesenchymal cells to the osteogenic lineage generated by bone matrix and particles, iPS cells require forced expression of transcription factors to enter these different lineages. iPS cells have the potential to be of great benefit in tissue repair and remodeling. Generation of host-derived iPS cells and transformation into cells needed for tissue repair, e.g. cardiomyocytes, into would provide host-transplant histocompatibility, eliminating the complications of tissue rejection. However, the challenges of using these cells are substantial. Recruitment to different fates can be difficult and lengthy, making them less than optimal for surgical repair of traumatic injury. In addition, studies have shown that iPS-derived cells are often transient, making repairs less than permanent, or that they produce tumours when implanted. To this end, the ability to generate stable, histocompatible differentiated cells in the host environment without the need for an intermediate transition to an iPS cell can provide a superior method of tissue repair and regeneration.

In contrast to the strides made in developing methods to induce bone repair and remodeling, neural repair has proved relatively intractable. Peripheral axonal regeneration can be achieved in some instances, particularly where regeneration requires growth over short distances, but repair of the central nervous system is still in its infancy. Embryonic stem cells and iPS cells can form neurons and a recent study of Caiazzo et al 2011 suggests that the direct conversion of fibroblasts to neurons is possible. However, methods of ensuring functional connectivity and regeneration of neuronal circuitry remain a challenge. As with induction of iPS cells, induction of neuronal differentiation requires the forced expression of transcription factors in isolated cells. Because demineralized bone matrix as well as microparticulate bone has the capacity for direct induction of osteogenic and chondrogenic cells, without requiring the forced expression of transcription factors. It was reasoned that there might be similar signals that could transduce the formation of neural cells from mesenchymal cells. To this end, a composition was implanted of non-viable microparticles from human spinal cord into nude rats and characterized the expression of a series of neuronal markers in host cells that colonize the spinal cord implants. Several markers of neuronal lineages, namely Olig2 and beta-III tubulin are expressed in host cells colonizing the spinal cord implants. These observations indicate the direct induction of neural precursors would provide additional avenues for engineering the repair of nervous system injury or disease. Induction of nerve tissue formation by embryonic neural crest without cellular participation was demonstrated in $1930^{th}$.

Materials and Methods: Implant preparation: Human post-mortem spinal cord without the dura mater was exercised aseptically from a cadaver donor through a posterior approach. The spinal cord was placed into lactated Ringer's solution and immediately transported to the laboratory where it was placed into the vapor phase of liquid nitrogen. The frozen spinal cord was transferred to the freeze-dryer with shelves pre-cooled to −30° C. and the external condenser to between −40 and −60° C. The vacuum was maintained at below 100 millitorr. After 3 days the shelves were heated to room temperature, vacuum released and the freeze-dried spinal cord removed. It was then cut into 0.5 cm pieces, and micronized in a Retsch cryomill into 100-400 micron particles. The entire procedure was conducted aseptically. Micronized spinal cord particles were sealed in glass containers in plastic bags. These were maintained at room temperature until implanted into animals.

Implant surgery: Freeze-dried spinal cord microparticles were implanted subcutaneously into nude rats, anesthetized with 5% inhaled isoflurane, then held at 2% isoflurane for the duration of the surgery. Small incisions were made parallel to the most caudal rib, and a cavity prepared by inserting a blunt probe rostrally under the skin. Spinal cord particle, either alone, or encased in hydroxyethyl starch to inhibit particle dispersion, were inserted into the cavity. Incisions were closed with wound staples and the animals returned to their cages for recovery. Implanted tissue was collected 2-4 weeks after surgery, and processed as described below. No difference was noted between isolated particles or hydroxyethyl starch-encased particles, so results from both are used interchangeably.

Tissue collection and processing, histology and immunohistochemistry: Spinal implants were collected 2-4 weeks after implantation. Implants were fixed overnight in Bouin's fluid, then dehydrated and embedded in paraffin and sectioned. 10 µm tissue sections were collected to prepared glass slides, dried overnight at 42° C., then used for histology or for immunohistochemistry. Immunohistochemistry was performed using antigen retrieval by boiling in Tris-HCl as described (Khialeeva et al., 2011). Primary antibody dilutions were as follows: anti-nestin (BD Biosciences), 1:300, anti-Olig2 (Millipore), 1:500, anti-Sox9 (Millipore) 1:500, anti-beta-III tubulin (Covance) 1:5000. Antibody-labeled sections were lightly counterstained with hematoxylin and eosin.

Sections were viewed on a Zeiss Axioskop and images collected using a cooled CCD camera with Axiovision software. Minor color adjustments to allow background matching were made using Adobe Photoshop.

Figure 1A:
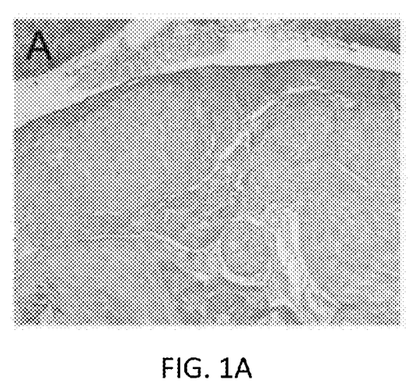
FIGS. 1A, 1B, 1E and 1F are photos of hematoxylin and eosin stained of one embodiment of the composition shown in photos 1A, 1B, 1E, 1F. It is noted
Figure 1B:
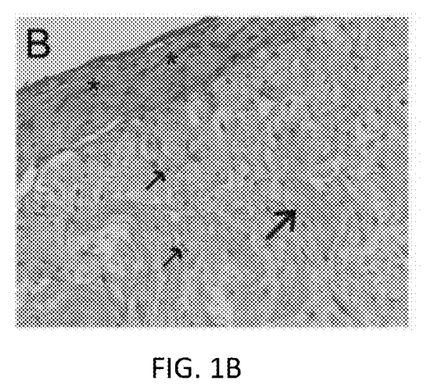
Figure 1E:
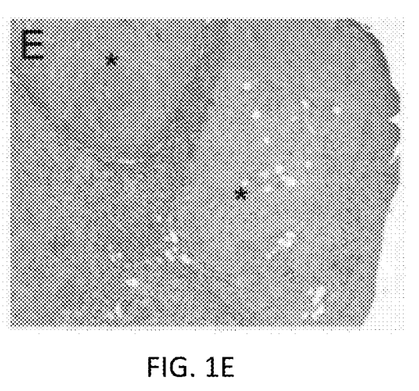
Figure 1F:
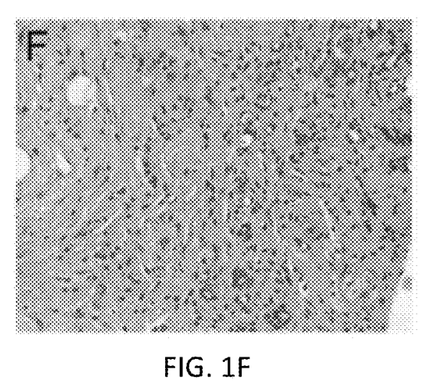

Test Results: Spinal cord implants, consisting of acellular microparticulate material, appear compact and easily distinguished from the surrounding tissue. Two weeks after implantation, the implants were surrounded by a defined border of elongated cells and appear to contain pockets of fibrillar material interspersed with small and medium-sized elongated cells (FIG. 1A, B). Some areas of fibrillar material appear to be infiltrated with cells, with cells more densely collected around the edges of the fibrillar regions and more sparsely in the center of these areas. The fibrillar material appears to be the remnants of the implanted human spinal cord particles, and the cellular distribution through this material resembles the pattern expected for infiltrating host cells. Four weeks after implantation, spinal cord implants were densely populated with cells. Fibrillar areas were still visible. Cell nuclei were evident throughout this material (FIG. 1E, F). At this stage, cells appear evenly distributed throughout the fibrillar regions, suggesting full dispersion of cells throughout these areas.

Figure 2A:
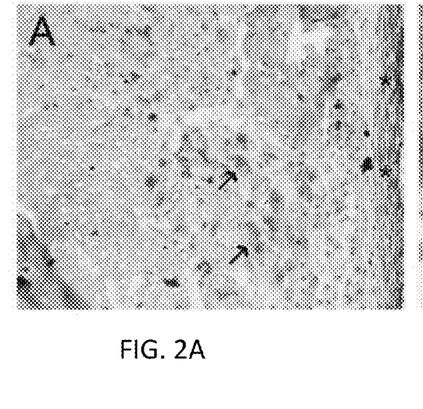
FIGS. 2A, 2B, 2C and 2E are photos of Nestin expression in spinal cord microparticles 2A, 2C, 2E at two weeks 2A, 2B and four weeks 2C, 2E after implantation. Asterisks in 2A indicate nestin positive margin cells and arrows indicate large nestin expressing cells. Arrow in 2B indicates nestin positive cells. At four weeks, spinal cord fibrillar material 2C, asterisk is surrounded by nestin positive cells 2C, arrows; nestin expression is also seen in cells within the fibrillar material 2E, arrows.
Figure 2B:
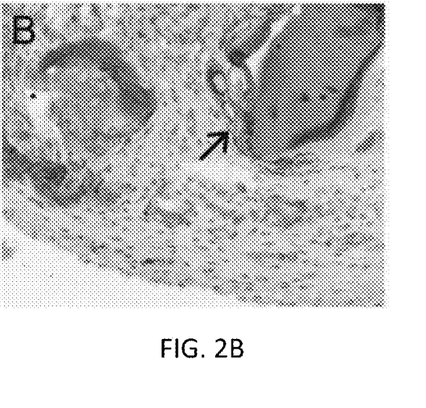
Figure 2C:
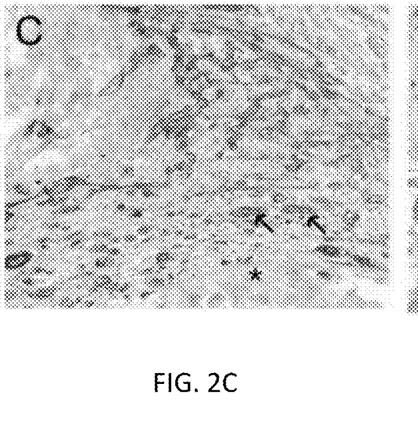
Figure 2E:
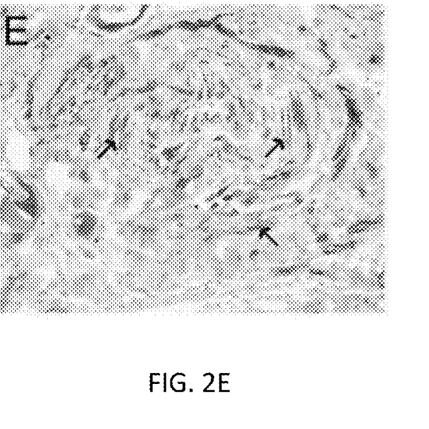
Figure 3A:
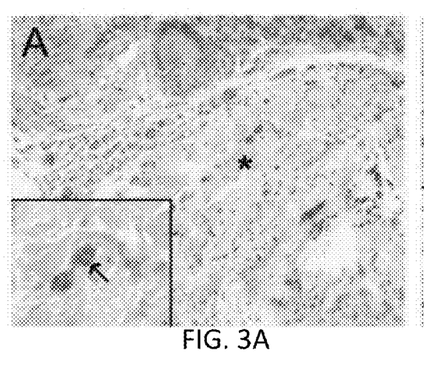
FIGS. 3A and 3C are photos of Olig2 expression in micronized spinal cord 3A, 3C implants at two weeks 3A and four weeks 3C. Olig2 is evident in nuclei 3A, arrow in inset in spinal cord implants and in cytoplasm, arrow in inset of cells colonizing particulate bone implants. Spinal cord fibrillar material 3C, arrow does not express Olig 2. Insets show higher magnification of representative cells.
Figure 3C:
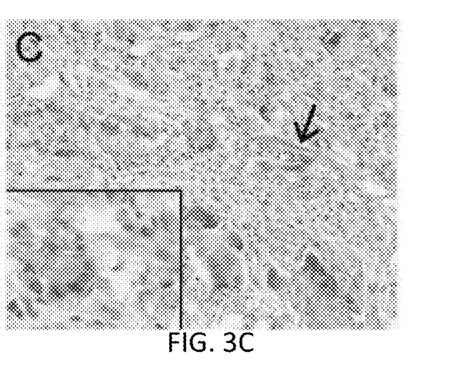
Figure 4A:
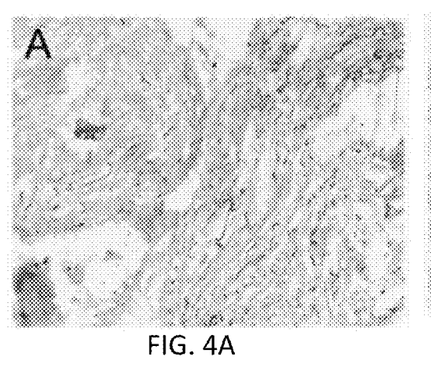
FIGS. 4A-4C are photos of beta-III tubulin in spinal cord 4A, 4C and particulate bone 4B implants at two weeks. Beta- III tubulin is evident inside large cells infiltrating the implanted spinal cord matrix 4C, arrows in inset.
Figure 4B:
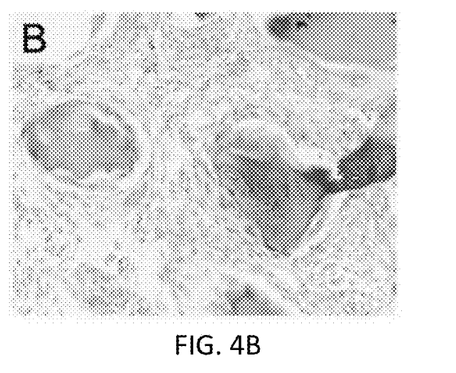
Figure 4C:
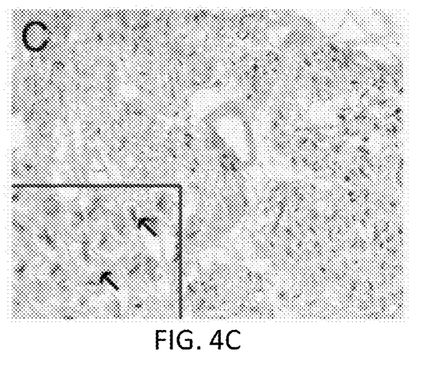
Figure 5A:
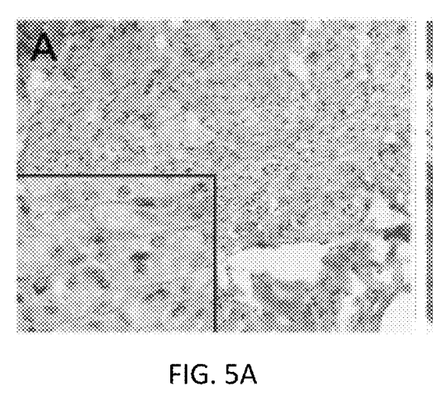
FIGS. 5A-5D are photos of Sox9 expression in micronized spinal cord 5A, 5C and particulate bone 5B, 5D implants at two weeks 5A, 5B and four weeks 5C, 5D. Sox9 is expressed at low levels in spinal cord implants (insets in 5A and 5C), but at high levels in both chondrocytes and matrix cells in particulate bone implants (insets in 5B and 5D). Insets in FIGS. 5A-5D show higher magnification of representative cells.
Figure 5B:
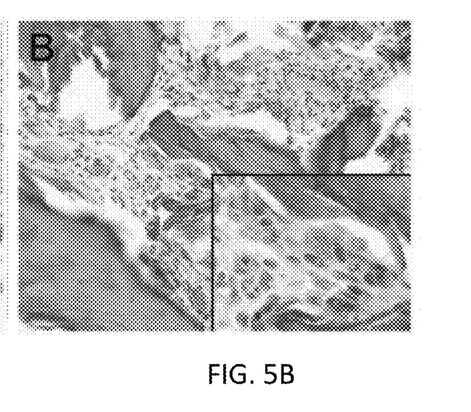
Figure 5C:
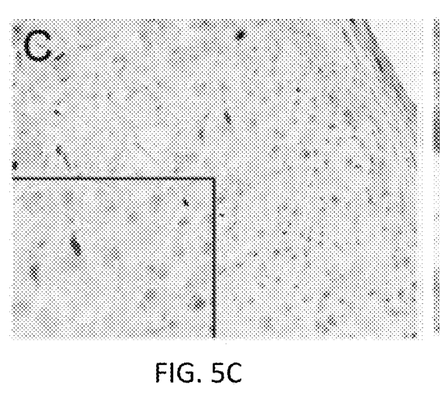
Figure 5D:
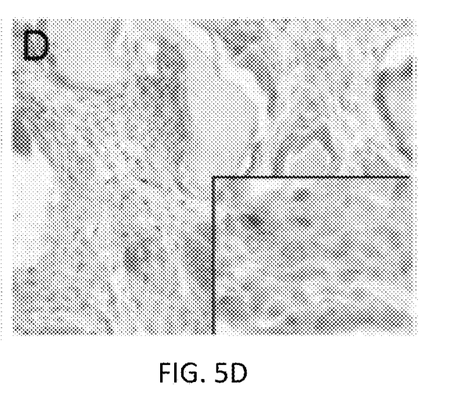

To determine the identity of the cells colonizing the spinal cord implants, immunohistochemistry with several cell-specific differentiation markers was relied upon. The expression of nestin, an early multi-lineage progenitor marker, Olig2, a neural/glial progenitor marker, and beta-III tubulin, a neural-specific cytoskeletal protein were determined. The expression of Sox9, a marker for early differentiating chondrocytes was also measured. Nestin expression was evident two weeks after implantation in several distinct populations of cells near the margins of the spinal cord implants (FIG. 2A). Along the outer edges of the implants, nestin expression was seen in the tightly packed cells defining the margins of the implants. Strong nestin expression was also seen in more loosely arranged cells deeper within the implants. After four weeks, nestin was extensively expressed in the spinal cord implants (FIG. 2C). Nestin was expressed at high levels in areas of loosely packed large cells and in elongated cells surrounding remnants of the spinal cord matrix. In some areas, nestin expression was interspersed with unlabeled fibrillar material (FIG. 2E). Several reports in the literature suggest that nestin is generically expressed in stem cells. Olig2, a transcription factor expressed early in neural/glial progenitors and later in cells restricted to an oligodendrocyte lineage, was expressed in spinal cord implants. Olig2 was widely expressed in cells surrounding domains of fibrillar material, as well as within cells that appear to be infiltrating the spinal cord fibrils (FIG. 3A). Subcellular localization of Olig2 changed from nuclear to cytoplasmic in the maturation of oligodendrocyte precursors during remyelination. By four weeks, Olig2 was widely expressed throughout the spinal cord implants, in large and small cells in all regions of the implants (FIG. 3C). As at two weeks, Olig2 was highly expressed in nuclei of cells colonizing the implant. Beta-III tubulin, a neuron-specific cytoskeletal protein, was expressed throughout the spinal cord implants (FIG. 4). beta-III tubulin was expressed in long filaments throughout the spinal cord implants, as well as in punctate bundles, which may represent cross-sectional profiles of filaments. Beta-III tubulin expression was observed both within regions of fibrillar material and in cells surrounding the fibrillar bundles. One possibility is that beta-III tubulin expression reflects residual beta-III tubulin in the implanted material. This is unlikely, as beta-III tubulin is clearly associated with cell profiles (FIG. 4C, inset), and the implanted material was acellular.

The present invention demonstrates the capacity of implanted microparticulate spinal cord material to recruit and initiate reprogramming of host cells. Host cells are visible in several domains surrounding implanted spinal cord material and exhibit several distinct morphologies. A layer of tightly packed elongated cells develops along the margins of the implanted material, potentially creating an isolation barrier around the implant. Host cells are evident infiltrating into the fibrillar material of the matrix, and over time spread throughout the implant, where they appear as large, loosely packed cells. Margin cells express nestin, while infiltrating cells express nestin, Olig2 and beta-III tubulin. These markers are indicative of cells with proliferative capacity and with the capacity to initiate differentiation into neuronal or glial lineages. Importantly, cells associated with the spinal cord implants show little to no expression of Sox9, a marker for early osteogenic differentiation. This suggests that spinal cord-derived, acellular material can induce the reprogramming of host cells into specific neural lineages. The present invention shows that host cells can be transformed into cells that express neural lineage. Host-derived neurons and glial cells may prove beneficial in repair after nerve injury, brain injury or stroke. Developing a histocompatible source of these cells has been a major goal of neural tissue engineering studies.

With reference to FIG. 8, sections from newly formed tissue induced by particulate spinal cord implants, 4 weeks post implantation are shown. Cell in the center of the photograph has characteristics of a bipolar neuron shown in FIG. 8A. It has clear nucleus prominent nucleolus, and elongated dark blue cytoplasm with axonal projections. The vesicular nucleus is round, and contains basophilic granules at its rim. Dark blue material in the cytoplasm represents Nissl substance (Nissl bodies) and is indicative of protein of the rough endoplasmic reticulum synthesized for neurotransmission. Romanowski-Giemsa stain, Xenon illumination X 1,600. With reference to FIG. 8B, newly formed cells in new tissue, formation of which was induced by particulate spinal cord implants. These cells contain Nissl substance demonstrable by thionin staining This again indicates neuronal nature of newly formed (induced) cells. Thionin, Xenon illumination X 1,600. With reference to FIG. 8C, high power view of newly formed cell stained with silver (arrow). Positive silver staining is an attribute of neuronal cells. Bodian stain, Xenon illumination X1600. With reference to FIG. 8D, newly formed neuronal cell has actively synthesized RNA, evidenced by orange-red fluorescence. Acridine orange. Hoffman modulation contrast. U.V. light with DM510 filter X400.

Preferred embodiments of this invention are described herein, including the best mode known to the inventor for carrying out the invention. Of course, variations of those preferred embodiments will become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modification equivalents of the subject matter recited in the claims appended hereto as permitted by applicable law. Moreover, any combination of the-above-described elements in all possible variations thereof is encompassed by the invention unless otherwise indicated herein or otherwise clearly contradicted by context.

What is claimed is:

1. A composition of dried neural tissue micronized particles or strands comprising spinal cord tissue harvested and excised without dura mater from a spinal cord of a mammal, the spinal cord tissue being dried or having the water content in the tissue reduced or eliminated by being dehydrated hypothermically, chemically or by freeze drying, cut into pieces, ground to form micronized particles or cut or chopped to form strands, prepared aseptically and sterile packaged in dose sized quantities, storable at room temperature to form the composition of dried neural tissue, the composition as processed forms an acellular material composition having an inductive capacity when implanted into human recipients to induce host cells to produce new neural tissue.

2. The composition of claim 1 wherein the spinal cord had been placed in lactated Ringer's Solution or other suitable fluid and placed into a vapor phase of liquid nitrogen and the frozen spinal cord was transferred to a freeze dryer under vacuum to remove water, at completion of drying cycle the freeze dryer was heated to room temperature to avoid moisture condensation and the vacuum released to form a freeze dried spinal cord.

3. The composition of claim of claim 1 wherein the spinal cord tissue was cut into pieces from a freeze dried spinal cord to form freeze dried spinal cord tissue pieces.

4. The composition of claim of claim 3 wherein the pieces of the freeze dried spinal cord tissue were ground to form freeze dried spinal cord tissue micronized particles or cut or chopped to form freeze dried spinal cord tissue strands which may be branched or fragments.

5. The composition of claim 4 wherein the freeze dried spinal cord tissue micronized particles have a particle size greater than 50 microns or the strands or fragments have a length in the range of 1 to 6 mm.

6. The composition of claim 5 wherein the particle size of the micronized particles is about 100 to about 400 microns or the length of the branched strands or fragments is about 2 to 4 mm.

7. The composition of claim 6 wherein the spinal cord tissue is harvested from vertebral column of the mammal.

8. The composition of claim 7 wherein the spinal cord tissue is harvested post mortem.

9. The composition of claim 8 wherein the mammal is one of a primate, an equine, a bovine, a porcine or other mammalian animals.

10. The composition of claim 9 wherein the primate is a human.

11. The composition of claim 10 wherein the human post mortem spinal cord was excised aseptically without dura mater from the cadaver donor.

12. A method of generating neural tissue growth in a human recipient comprises the steps of:
providing a composition of dried neural tissue micronized particles or strands having spinal cord tissue harvested and excised without dura mater from a spinal cord of a mammal, the spinal cord tissue being dried or having the water content in the tissue reduced or eliminated by being dehydrated hypothermically, chemically or by freeze drying, cut into pieces, ground to form micronized particles or cut or chopped to form strands, prepared aseptically and sterile packaged in dose sized quantities, storable at room temperature to form the composition of dried neural tissue, the composition as processed forms an acellular material composition having an inductive capacity when implanted into human recipients to induce host cells to produce new neural tissue; and
implanting one or more doses of the composition wherein the freeze dried spinal cord tissue micronized particles or strands or fragments or combinations thereof are implanted into human recipients having neural cell or nerve damage.

13. The method of claim 12 wherein the implanted composition of spinal cord tissue micronized particles or strands or fragments or combinations thereof after implantation initiates a cellular response of host cells and a reprogramming of host cells.

14. The method of claim 13 wherein host cells infiltrate the composition and spread throughout the composition to form infiltrating host cells.

15. The method of claim 14 wherein the infiltrating host cells exhibit and express nestin, Olig2 and beta-III tubulin markers with the capacity to initiate differentiation into neuronal or glial lineages.

16. The method of claim 15 wherein the infiltrating host cells associated with the implanted composition have no expression of the marker Sox9 for osteogenic differentiation.

17. The method of claim 16 wherein the freeze dried spinal cord tissue is processed to form an acellular material composition with the capacity to induce reprogramming of host cells into specific neural lineages.

18. The method of claim 17 wherein the freeze dried spinal cord tissue when used as an implant transforms host cells to express neural lineage markers in the absence of forced reprogramming of host cells by expressed transcription factor needed to drive neural differentiation.

19. The method of claim 18 wherein the freeze dried spinal cord tissue when used in an implant can be used as a neural treatment for repair of brain injury due to trauma or stroke or as a neural treatment for degenerative neural conditions.

20. The method of claim 19 wherein the implant can be used to promote repair of nerve damage or to stimulate new nerve growth or both.

21. The composition of claim 1 wherein the spinal cord tissue was provided as fragments.

22. The composition of claim 21 wherein the fragments were freeze dried.

23. The composition of claim 22 wherein the fragments were embedded in a bioabsorbable material for implantation.

24. The composition of claim 23 wherein the bioabsorbable material was a hydroxyethyl starch.

25. A composition of dried neural tissue micronized particles or strands comprising spinal cord tissue harvested and excised without dura mater from a spinal cord of a mammal, the spinal cord tissue being dried or having the water content in the tissue reduced or eliminated by being dehydrated hypothermically, cut into pieces, ground to form micronized particles or cut or chopped to form strands, prepared aseptically and sterile packaged in dose sized quantities, storable at room temperature to form the composition of dried neural tissue, the composition as processed forms an acellular material composition having an inductive capacity when implanted into living mammal recipients to induce host cells to produce new neural tissue wherein the spinal cord tissue is prepared by dehydration at hypothermic temperatures.

26. The composition of claim 1 wherein the spinal cord tissue is chemically dehydrated.

27. The composition of claim 1 wherein the spinal cord tissue is rehydrated prior to implantation.

* * * * *